March 6, 1956 H. C. SWIM Plant Pat. 1,458
ROSE PLANT
Filed March 7, 1955
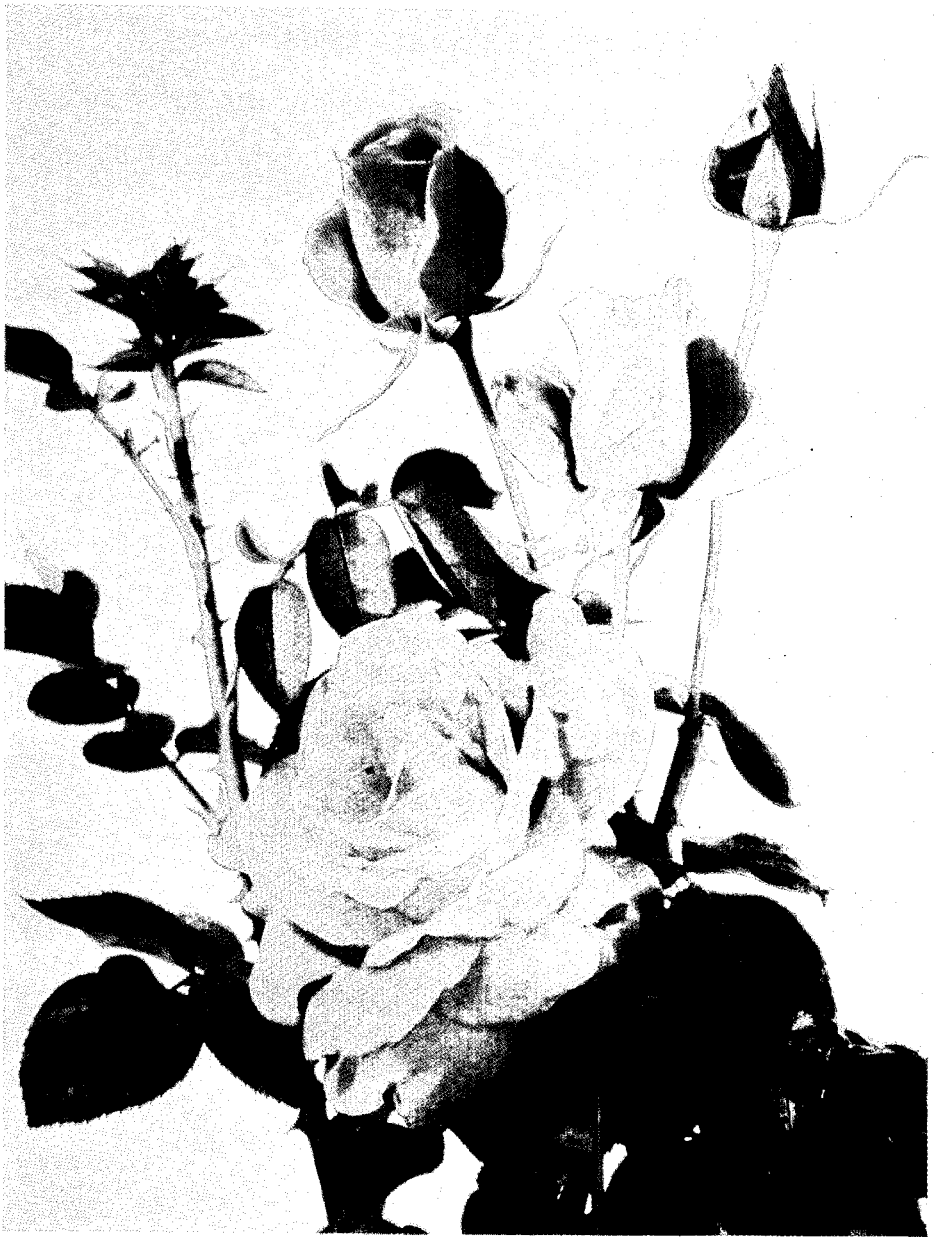
Inventor.
H. C. Swim
By: Robb & Robb
Attorneys.

United States Patent Office

Plant Pat. 1,458
Patented Mar. 6, 1956

1,458

ROSE PLANT

Herbert C. Swim, Ontario, Calif., assignor to Armstrong Nurseries, Inc., Ontario, Calif., a corporation of California Application March 7, 1955, Serial No. 492,818

1 Claim. (Cl. 47—61)

The present invention relates to a new and distinct variety of rose plant of the hybrid tea class, which was originated by me by crossing the well-known varieties "Charlotte Armstrong" (Plant Patent No. 455) and "Red Jacket" (Plant Patent No. 968).

The primary objective in this breeding was to produce a new rose variety which combines the most desirable characteristics of the parent varieties. This objective was fully achieved, as evidenced by the following unique combination of outstanding features of the new variety:

(1) The abundant foliage which covers the plant well;

(2) The urn shape of the buds;

(3) The longer than average flowering stems, as inherited from the parent variety "Charlotte Armstrong";

(4) The large size of the blooms, a characteristic which is also inherited from "Charlotte Armstrong";

(5) A petal substance approaching that of the parent variety "Red Jacket," with attendant long-lasting quality of the bloom color which is especially outstanding among hybrid tea varieties in or near the color range of the flower color of the new variety;

(6) The large size of the individual petals of the blooms, said petals being similar in size to those of the parent variety "Charlotte Armstrong," but broader in relation to their length, and having a shape similar to those of the parent variety "Red Jacket"; and (7) The distinctive bloom color which is a medium to dark shade of red and similar to the color of the blooms of "Red Jacket."

In comparison with its seed parent "Charlotte Armstrong," the bloom color of my new variety is a medium to dark shade of red, whereas the bloom of color of this parent is a light shade of red, popularly described as spectrum red to cerise; the buds of the new variety are a pronounced urn-shape, whereas those of this variety are longer and more pointed, with only a slight tendency toward urn shape; the flower petals of the new variety are broader in relation to their length than those of this parent; and the number of petals of the flowers of the new variety ranges from 18 to 25, whereas the petal range of "Charlotte Armstrong" is from 25 to 35.

As compared with its pollen parent "Red Jacket," the blooms of my new variety are substantially larger in size than those of this parent; the petals of the blooms are substantially larger than those of this parent, with the outer petals being broader and more rounded at their base; the flowering stems of the new variety are longer than those of "Red Jacket" and are less prone to cluster; the foliage of the new variety is more abundant and covers the plant better than the foliage of "Red Jacket"; and the color of the foliage of the new variety is a somewhat lighter shade of green.

The foregoing characteristics and distinctions definitely differentiate my new variety from its patents, as well as from all other varieties of its class of which I am aware, and asexual reproduction of the new variety by budding, as performed at Ontario, California, shows that said characteristics and distinctions come true to form and are established and transmitted through succeeding propagations.

The accompanying drawing shows typical specimens of the flowers, foliage and stems of the new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Charlotte Armstrong,"

*Pollen parent.*—"Red Jacket."

Propagation: Holds its distinguishing characteristics through succeeding propagations by budding.

FLOWER

Locality where grown and observed: Ontario, California.

Flowers borne: Usually singly, but sometimes 2 or 3 to the stem; on long stems of medium length and from normal strength to strong.

Quantity of bloom: Free, outdoors.

Continuity: Nearly continuous during growing season.

Fragrance: Slight.

Bud:

*Peduncle.*—Long; average caliper; erect; smooth; some gland-tipped cilia. Color—near Biscay Green, Plate XVII (Ridgway), overlaid somewhat with near Deep Corinthian Red, Plate XXVII (Ridgway) on side exposed to the sun.

*Before calyx breaks.*—Size—medium. Form—medium length; ovoid; with foliaceous appendages; usually glabrous; usually with slender foliaceous parts extending beyond the tip of the bud equal to ¼ or more of its length.

*As calyx breaks.*—Color—near Cardinal Red, Plate 822/1, page 168 (Wilson), shaded somewhat with near Chrysanthemum Crimson, Plate 824/2, page 169 (Wilson).

*Sepals.*—Inner surface with fine, woolly tomentum; margins of alternate sepals lined with fine, woolly tomentum; others lined with gland-tipped cilia and hairs.

*As first petal opens.*—Size—large. Form—long; urn-shaped. Color: Outside—near Cardinal Red, Plate 822/2, page 168 (Wilson), marked somewhat with near Rose Red, Plate 724, page 158 (Wilson); inside—between Cherry, Plate 722, page 157 (Wilson) and Currant Red, Plate 821/1, page 167 (Wilson).

*Opening.*—Opens up well; is not retarded from opening by cold, hot, wet or dry weather.

Bloom:

*Size (when fully open).*—Large; from 5 inches to 6 inches.

*Petalage.*—Semi-double; from 18 to 25 petals, plus 3 to 8 petaloids; arranged regularly.

*Form.*—High-centered at first, but becoming open later; petals at first being cupped, with lateral margins of outer petals reflexed from ½ to ⅔ of petal length, and with apex of outer petals sometimes reflexed from ⅓ to ½ of petal length; lateral margins of inner petals occasionally reflexed slightly from ⅛ to ¼ of petal length, with apex of inner petals sometimes reflexed approximately ⅛ of petal length; becoming later at maturity flat-cupped, with lateral margins of petals usually reflexed from ¾ to the entire length of the petals, and with apex sometimes reflexed from ⅛ to ¼ of the petal.

Petals:

*Texture.*—Thick; leathery; with inside velvety and outside satiny.

*Shape.*—Outside—broadly obovate, with apex flat, and sometimes with 1 or 2 notches. Intermediate—obovate, with apex from rounded to flat, and sometimes with 1 or 2 notches. Inside—obovate, but sometimes irregular, with apex rounded and having 1 or 2 notches.

This description of a newly opened flower was made from a rose grown outdoors in the month of October, at Ontario, California:

Color:

*Outside petal.*—Outside surface—between Rose Red, Plate 724, page 158 (Wilson) and Cardinal Red, Plate 822/3, page 168 (Wilson); small area at base of petal near attachment near Lemon Yellow, Plate 4/2, page 4 (Wilson). Inside surface—between Cherry, Plate 722, page 157 (Wilson) and Current Red, Plate 821/2, page 167 (Wilson); small area at base of petal near attachment near Lemon Yellow, Plate 4/2, page 4 (Wilson).

*Intermediate petal.*—Outside surface—between Rose Red, Plate 724, page 158 (Wilson) and Cardinal Red, Plate 822/3, page 168 (Wilson); small area at base of petal near attachment near Lemon Yellow, Plate 4/2, page 4 (Wilson). Inside surface—between Cherry, Plate 722, page 157 (Wilson) and Currant Red, Plate 821/2, page 167 (Wilson); small area at base of petal near attachment near Lemon Yellow, Plate 4/2, page 4 (Wilson).

*Inner petal.*—Outside surface—between Rose Red, Plate 724, page 158 (Wilson) and Cardinal Red, Plate 822/3, page 168 (Wilson); small area at base of petal near attachment near Lemon Yellow, Plate 4/2, page 4 (Wilson). Inside surface—near Cherry, Plate 722, page 157 (Wilson), shaded only slightly with near Currant Red, Plate 821/3, page 167 (Wilson); small area at base of petal near attachment near Lemon Yellow, Plate 4/2, page 4 (Wilson).

This description was made from a rose that was open for 3 days outdoors in the month of October, at Ontario, California:

Color:

*Outside petal.*—Outside surface—between Rose Red, Plate 724/1, page 158 (Wilson) and Tyrian Purple, Plate 727/1, page 159 (Wilson); small area at base of petal near attachment near Aureolin, Plate 3/2, page 3 (Wilson). Inside surface—near Rose Red, Plate 724, page 158 (Wilson); small area at base of petal near attachment near Aureolin, Plate 3/2, page 3 (Wilson).

*Inside petal.*—Outside surface—near Rose Red, Plate 724/1, page 158 (Wilson); small area at base of petal near attachment near Aureolin, Plate 3/2, page 3 (Wilson). Inside surface—near Rose Red, Plate 724, page 158 (Wilson); small area at base of petal near attachment near Aureolin, Plate 3/2, page 3 (Wilson).

General color effect:

*Newly opened flower.*—Between Cherry, Plate 722, page 157 (Wilson) and Currant Red, Plate 821/1, page 167 (Wilson).

*3-days open.*—Near Rose Red, Plate 724, page 158 (Wilson).

Behavior: Drop off cleanly; not particularly affected by cold, hot, wet or dry weather.

Flower longevity: On bush in garden—3 or 4 days in November. Cut roses grown outdoors and kept at living-room temperatures—4 days in November.

REPRODUCTIVE ORGANS

Stamens: Average number; arranged regularly about pistils.

Filaments: Long; from 10 to 18 mm. in length; most with anthers.

*Color.*—Between Crimson, Plate 22/2, page 22 (Wilson) and Camellia Rose, Plate 622/1, page 148 (Wilson).

Anthers: Medium size; all open approximately at once.

*Color.*—Upper side—margins between Buttercup Yellow, Plate 5/2, page 5 (Wilson) and Indian Yellow, Plate 6/2, page 6 (Wilson); remainder near Empire Yellow, Plate 603/3, page 66 (Wilson); inner portion sometimes very lightly overlaid with near Carmine, Plate 21/3, page 21 (Wilson). Under side—margins between Buttercup Yellow, Plate 5/2, page 5 (Wilson) and Indian Yellow, Plate 6/2, page 6 (Wilson); remainder near Empire Yellow, Plate 603/3, page 66 (Wilson); inner portion sometimes very lightly overlaid with near Carmine, Plate 21/3, page 21 (Wilson).

Pollen: Moderate quantity.

*Color.*—Near Buttercup Yellow, Plate 5/2, page 5 (Wilson).

Pistils: Average number; approximately 70 in number.

Styles: Moderately even; from short to average length; from 5 to 10 mm. in length; average caliper; bunched.

*Color.*—Lower ⅔ of style between Uranium Green, Plate 63/3, page 63 (Wilson) and Dresden Yellow, Plate 64/3, page 64 (Wilson); upper ⅓ of style near Currant Red, Plate 821/2, page 167 (Wilson).

Stigma:

*Color.*—Near Empire Yellow, Plate 603/3, page 66 (Wilson).

Ovaries: Most enclosed in calyx, but some protruding from calyx.

Hips: None.

Sepals: Permanent; long; recurved.

*Colors*—inside—near Biscay Green, Plate XVII (Ridgway), masked by white woolly tomentum. Outside—between Light Elm Green, Plate XVII (Ridgway) and Bice Green, Plate XVII (Ridgway).

Seeds: None.

PLANT

Foliage:

*Leaves.*—Compound of usually 5 to 7 leaflets; from normal number to abundant; from medium size to large; leathery; non-glossy.

*Leaflets.*—Shape—ovoid, with apex acute. Base—round. Margin—simply serrate.

*Color.*—Mature: Upper surface—near Forest Green, Plate XVII (Ridgway); under surface—between Chromium Green, Plate XXXII (Ridgway) and Clear Fluorite Green, Plate XXXII (Ridgway). Young: Upper surface—between Chromium Green, Plate XXXII (Ridgway) and Deep Dull Yellow Green, (1) Plate XXXII (Ridgway), overlaid particularly around margins with Dark Indian Red, Plate XXVII (Ridgway); under surface—near Turtle Green, Plate XXXII (Ridgway), overlaid with between Mineral Red, Plate XXVII (Ridgway) and Indian Red, Plate XXVII (Ridgway).

*Rachis (the supporting stem of the compound leaf).*—Average size. Upper side—grooved; hairy, some stipitate glands on edges. Under side— smooth; with few stipitate glands; rarely with 1 or 2 prickles.

*Stipules.*—From medium length to long; medium width; with medium length points turning out at an angle of more than 45°.

*Disease resistance.*—Average resistance to mildew as compared with other varieties grown under comparable cultural conditions, at Ontario, California.

Growth:

*Habit.*—Bushy; upright; moderately branched.

*Growth.*—Vigorous.

*Canes.*—Medium caliper.

*Main stems.*—Color—between Spinach Green, Plate V (Ridgway) and Parrot Green, Plate VI (Ridgway). Large prickles—several; from short to medium length; almost straight; with long, narrow base. Color—between Drab-Gray, Plate XLVI (Ridgway) and Smoke Gray, Plate XLVI (Ridgway). Small prickles — from few to several. Color—near Drab-Gray, Plate XLVI (Ridgway). Hairs—none.

*Branches.*—Color—between Biscay Green, Plate XVII (Ridgway) and Bice Green, Plate XVII (Ridgway). Large prickles—several; from short to medium length; almost straight; with long, narrow base. Color — between Russet, Plate XV (Ridgway) and Cinnamon Brown, Plate XV (Ridgway). Small prickles—several. Color—between Russet, Plate XV (Ridgway) and Cinnamon Brown, Plate XV (Ridgway). Hairs.—none.

*New shoots.*—Color—between Courge Green, Plate XVII (Ridgway) and Biscay Green, Plate XVII (Ridgway), overlaid with near Indian Red, Plate XXVII (Ridgway). Large prickles—from several to many; medium length; almost straight; with long, narrow base. Color—between Mineral Red, Plate XXVII (Ridgway) and Indian Red, Plate XXVII (Ridgway). Small prickles — several. Color—between Mineral Red, Plate XXVII (Ridgway) and Indian Red, Plate XXVII (Ridgway). Hairs—None.

I claim:

A new and distinct variety of rose plant of the hybrid tea class, substantially as herein shown and described, characterized particularly as to novelty by its abundant foliage which covers the plant well, its prominently urn-shaped buds, its longer than average flowering stems, its large blooms, the large size and relatively broad individual petals of its blooms, with the petal shape similar to that of the variety "Red Jacket" (Plant Patent No. 968), the good petal substance approaching that of the variety "Red Jacket," with attendant long-lasting quality of the bloom color, and the distinctive color of the blooms varying between medium and dark shades of red color.

No references cited.